United States Patent [19]

Berger et al.

[11] 4,282,212

[45] Aug. 4, 1981

[54] IMMUNE-STIMULATING 1-(N-ACYLCARBAMOYL)-2-CYANOAZIRIDINES

[75] Inventors: Herbert Berger, Mannheim-Käfertal; Rudi Gall, Hirschberg-Grossachsen; Wolfgang Kampe, Heddesheim; Uwe Bicker, Mannheim; Gottfried Hebold, Mannheim-Vogelstang, all of Fed. Rep. of Germany

[73] Assignee: Boehringer Mannheim GmbH, Mannheim, Fed. Rep. of Germany

[21] Appl. No.: 838,426

[22] Filed: Sep. 30, 1977

[30] Foreign Application Priority Data

Oct. 5, 1976 [DE] Fed. Rep. of Germany ....... 2644820
Jun. 18, 1977 [DE] Fed. Rep. of Germany ....... 2727550

[51] Int. Cl.³ ................ C07D 203/20; A61K 31/395; C07F 9/22; C07F 9/24
[52] U.S. Cl. .............................. 424/200; 260/239 E; 260/239 EP; 260/326 A; 260/326.37; 260/346.73; 260/347.3; 260/340.5 R; 544/111; 544/238; 546/156; 546/208; 546/275; 548/186; 548/200; 548/248; 548/336; 544/59; 424/244; 424/282
[58] Field of Search ...... 260/239 E, 239 EP, 340.5 R; 424/200, 282, 244

[56] References Cited

U.S. PATENT DOCUMENTS 3,406,192  10/1968  Speziale ............. 260/239 E

OTHER PUBLICATIONS

Bicher, Chem. Abs. 86, 101148k (1977).
Bicher, Chem. Abs. 83, 201842p (1975).

*Primary Examiner*—Mark L. Berch
*Attorney, Agent, or Firm*—Sprung, Felfe, Horn, Lynch & Kramer

[57] ABSTRACT

1-(N-Acyl-carbamoyl)-2-cyanoaziridines of the formula

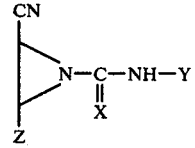

wherein
X is oxygen or sulphur,
Z is hydrogen or an organic radical, and
Y is a carbonyl, sulphonyl, sulphinyl, sulphenyl, phosphoryl or phosphonyl radical, and salts thereof, exhibit immune-stimulating and cancerostatic activities.

11 Claims, No Drawings

IMMUNE-STIMULATING 1-(N-ACYLCARBAMOYL)-2-CYANOAZIRIDINES

The present invention is concerned with new 1-(N-acylcarbamoyl)-2-cyanoaziridines and with the preparation thereof.

It is known from German Democratic Republic Pat. No. 110,492 that 1-acyl-2-cyanoaziridines are cystostatically active. 1-Carbamoyl-2-cyanoaziridine, mentioned by way of example, brings about, when administered intravenously to rats, a considerable increase in the leucocytes and lymphocytes, whereas the number of erythrocytes remains almost unchanged. Furthermore, a considerable increase of the antibody-forming spleen cells is observed. Therefore, this compound can also be used as an immune-stimulating therapeutic substance in the case of attack by pathogenic micro-organisms, for example, in the case of bacterial, viral, fungal and protozoal infections (see Federal Republic of Germany Pat. Specification DOS No. 25 28 460). However, the low stability of this compound in solution and its complete ineffectiveness when administered orally are severe disadvantages.

Consequently, there is a need to find cancerostatic and immune-stimulating therapeutic compounds which, with the same or better effectiveness and with a low toxicity, are more stable and, therefore, can be more simply administered, preferably orally.

We have now found a group of 1-carbamoyl-2-cyanoaziridine compounds which are substituted on the carbamoyl nitrogen atom by an additional acyl radical and in which the carbamoyl oxygen atom can also be replaced by a sulphur atom, which solve the problem.

Thus, according to the present invention, there are provided 1-(N-acylcarbamoyl)-2-cyanoaziridines of the general formula:

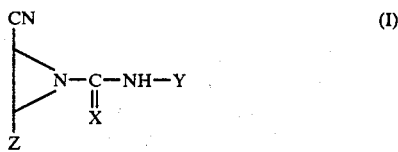

wherein X is an oxygen or sulphur atom, Z is a hydrogen atom or an alkyl radical containing up to 4 carbon atoms or a phenyl radical and Y is a $-CO-R_1$, $-SO_2-R_2$, $-SO-R_3$, $-S-R_3$ or

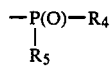

radical, $R_1$ is a hydrogen atom or a nitrile group or a lower alkoxy, alkoxycarbonyl or N,N-dialkylaminocarbonyl radical or a lower N-alkyl-N-phenyl or N,N-dialkylamino radical, or $R_1$ is a saturated or unsaturated aliphatic hydrocarbon radical which can be substituted one or more times by halogen, nitrile or lower N-acylamino, N,N-dialkylamino, alkoxy, alkoxycarbonyl, acyloxy, N,N-dialkylaminocarbonyloxy, alkylsulphonyl or alkylthio radicals or by phenyl, naphthyl, phenylthio or phenoxy radicals, which can be substituted by halogen, nitro, phenyl, lower alkyl, alkoxy or alkylthio radicals, or by lower dialkoxyphosphoryloxy or dialkoxyphosphono radicals, or by cycloalkyl, N-succinimido or N-phthalimido radicals or by aromatic heterocyclic radicals which can be substituted one or more times by halogen, nitro, phenyl, nitrile, trifluoromethyl, lower alkyl, alkoxy, alkoxycarbonyl, alkylsulphonyl, alkylthio or acyloxy radicals, or by radicals of the general formula:

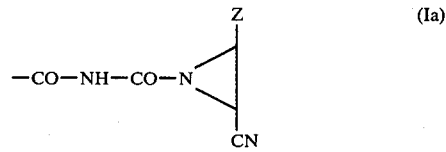

or $R_1$ is a phenyl, phenoxy or optionally hydrogenated naphthyl radical, which can be substituted one or more times by halogen, trifluoromethyl, sulphamoyl, nitro, nitrile, phenyl, lower alkyl, N-acylamino, alkylthio, alkylsulphonyl, alkoxy, alkoxycarbonyl, alkoxycarbonylalkyl, N,N-dialkylamino, N,N-dialkylaminocarbonyl, N,N-dialkylaminocarbonylalkyl, acyl, acyloxy or acyloxyalkyl radicals or by methylenedioxy radicals or by radicals of general formula (Ia), or $R_1$ is a cycloalkyl or saturated or aromatic heterocyclic radical, which can be substituted one or more times by halogen, nitro, nitrile, trifluoromethyl, phenyl, lower alkyl, alkoxy, alkoxycarbonyl, alkylthio, acyloxy or alkylsulphonyl radicals; $R_2$ is a lower saturated or unsaturated aliphatic hydrocarbon radical, which can be substituted one or more times by halogen atoms, lower alkoxycarbonyl or acyloxy radicals, or $R_2$ is a cycloalkyl, amino or lower dialkylamino radical or a phenyl radical, which can be substituted one or more times by lower alkyl or alkoxy radicals, halogen atoms or nitro groups or by radicals of general formula:

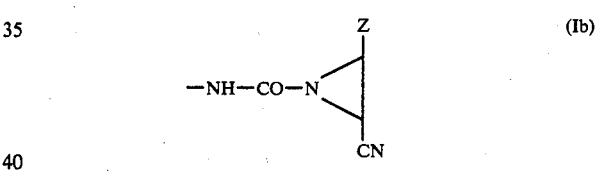

or $R_2$ is a radical of general formula (Ib) or $R_2$ is a saturated or aromatic heterocyclic radical, which can be substituted one or more times by halogen, nitro, nitrile, trifluoromethyl, phenyl, lower alkyl, alkoxy, alkylsulphonyl, acyloxy, alkylthio or alkoxycarbonyl radicals; $R_3$ is a lower alkyl or trifluoromethyl radical or a phenyl radical, which can be substituted one or more times by lower alkyl, acyloxy, alkylthio, alkylsulphonyl, alkoxycarbonyl or alkoxy radicals, halogen atoms or trifluoromethyl or nitro radicals; and $R_4$ and $R_5$, which can be the same or different, are lower alkyl or alkoxy radicals or phenyl or phenoxy radicals, which can be substituted by halogen, lower alkyl or alkoxy radicals, or the radical of general formula (Ib), or $R_4$ and $R_5$ together also represent an alkylenedioxy radical containing up to 4 carbon atoms; and the pharmacologically compatible salts thereof.

The 1-(N-acylcarbamoyl)-2-cyanoaziridines of general formula (I) are, therefore, N-acyl compounds, the acyl radical of which is derived from a carboxylic, sulphonic, sulphinic, sulphenic, phosphonic or phosphoric acid.

Insofar as not otherwise stated, the alkyl radicals of the substituents $R_1$, $R_2$, $R_3$, $R_4$ and $R_5$, whether alone or in combination, for example in alkoxy, alkoxycarbonyl, alkylthio, alkylsulphonyl, N-alkylamino, N,N-dialkylamino, acyloxy, N-acylamino, dialkoxyphosphoryloxy or dialkyloxyphosphono radicals, are radicals containing up to 6 and preferably up to 4 carbon atoms, which can be straight-chained or branched but are preferably methyl or ethyl radicals.

The lower acyl radicals of the substitutents $R_1$, $R_2$ and $R_3$, whether alone or in combination, for example in acyloxy or N-acylamino radicals, are residues of organic acids and preferably of alkyl-carboxylic acids, arylcarboxylic acids and the corresponding sulphonic acids, the acetyl and benzoyl radicals being preferred.

The saturated or unsaturated, straight-chained or branched aliphatic hydrocarbon radicals of the substituents $R_1$ and $R_2$, which can possibly also be substituted, can contain up to 12 carbon atoms. The substituted saturated aliphatic hydrocarbon radicals are preferably —$CH_2$— or —$CH_2$—$CH_2$— radicals and the substituted unsaturated aliphatic hydrocarbon radical is preferably the —CH=CH— radical.

By halogen, there is to be understood, according to the present invention, fluorine, chlorine, bromine and iodine, fluorine and chlorine being preferred.

The cycloalkyl radicals of the substituents $R_1$ and $R_2$ are preferably cyclopropyl, cyclobutyl, cyclopentyl, cyclohexyl, cycloheptyl or cyclooctyl radicals.

The saturated heterocyclic radicals of the substituents $R_1$ and $R_2$ are to be understood to be preferably 5-and 6-membered ring systems with one or more hetero atoms, for example oxygen, sulphur or nitrogen atoms, which ring systems can be substituted by a lower alkyl radical, the pyrrolidine, piperidine, piperazine and morpholine radicals being preferred.

The aromatic heterocyclic radicals of the substituents $R_1$ and $R_2$ are to be understood to be preferably 5- and 6-membered ring systems with one or more hetero atoms, for example oxygen, sulphur or optionally alkylated nitrogen atoms, which can also be fused with a benzene ring.

Preferred heteroaromatic ring systems include furan, thiophene, thiazole, imidazole, pyrazole, pyrrole, pyridine, pyrazine, pyrimidine, pyridazine, benzothiophene, benzofuran, benzthiazole, indole, isoxazole and quinoline. Preferred substituted heterocyclic ring systems according to the present invention include 1-methyl-3-nitropyrazole, 2-methyl-thiazole, 1-methyl-5-nitroimidazole, 3-cyanopyridine, 2-methylbenzthiazole, 2-nitrofuran, 2-methylsulphonylfuran, 2-chloropyridine, 3-methoxypyridazine, 3-methylthiopyridazine, 2,3-dichlorothiophene, 4-ethoxycarbonylpyridine, 3-nitrothiophene, 2-methylthiophene and 3-phenyl-5-methyl-isoxazole radicals.

The hydrogenated naphthyl radical is preferably the tetrahydronaphthyl radical.

The compounds according to the present invention can be prepared, for example, by the reaction of 2-cyanoaziridine of the general formula:

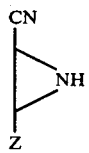
(II)

wherein Z has the same meaning as above, with an isocyanate or isothiocyanate of the general formula:

(III)

wherein X and Y have the same meanings as above, or with a diisocyanate of the general formula:

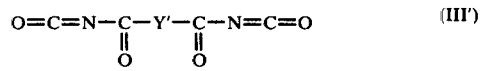
(III')

wherein Y' is an alkylene radical containing up to 12 carbon atoms or a phenylene radical, or with a diisocyanate of the general formula:

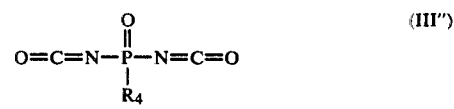
(III'')

wherein $R_4$ has the same meaning as above, in an inert solvent.

The 3-substituted 2-cyanoaziridines of general formula (II) can be prepared by known methods, preferably by brominating appropriately 3-substituted acrylonitriles and reacting the 2,3-dibromopropionitriles obtained with ammonia.

Some of the isocyanates and isothiocyanates of general formula (III) are new compounds which can be prepared by known methods. For the preparation of the isocyanates, an appropriate acid amide is preferably reacted with oxalyl chloride in an inert solvent, for example methylene chloride or ethylene chloride, generally by boiling under reflux. Another method of preparation starts from an appropriate acid chloride which is then reacted with silver isocyanate. The isothiocyantes are preferably prepared by reacting an appropriate acid chloride with a thiocyanate, for example potassium thiocyanate.

The inert solvents used can be, for example, aromatic hydrocarbons, such as toluene or benzene, or ethers, such as diethyl ether, dioxane or tetrahydrofuran.

The reaction can be carried out at a temperature of from 0°–100° C. or at the boiling point of the solvent used, although usually the reaction can be satisfactorily carried out at ambient temperature.

Furthermore, the compounds of the present invention can be prepared by the following reactions:

1. Reaction of an α,β-dihalopropionitrile of the general formula:

(IV)

wherein Z has the same meaning as above and Hal is a chlorine or bromine atom, with an acyl-urea or an acyl-thiourea of the general formula:

(V)

wherein X and Y have the same meanings as above, in the presence of an acid-binding agent, for example of a tertiary amine or of an alkali metal or alkaline earth metal hydroxide or carbonate. The reaction is carried out in an inert solvent, for example, in an aromatic hydrocarbon or ether or in dimethyl formamide or dimethyl sulphoxide, at a temperature between ambient temperature and the boiling point of the solvent. As solvent there can, however, preferably be used an excess of the tertiary amine which simultaneously serves as acid-binding agent.

2. Reaction of an acrylonitrile derivative of the general formula:

Z—CH=CH—CN       (VI)

wherein Z has the same meaning as above, with an azide of the general formula:

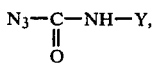
       (VII)

wherein Y has the same meaning as above. The reaction is preferably carried out by dry heating of the reaction mixture, nitrogen being split off from the azide (VII) to give the corresponding nitrene, which then condenses with the acrylonitrile derivative (VI).

3. Reaction of a 1-carbamoyl-2-cyanoaziridine of the general formula:

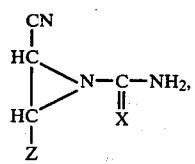
       (VIII)

wherein X and Z have the same meanings as above, with an active derivative of an acid of the general formula HOY, wherein Y has the same meaning as above, under the same conditions as in process 1. The active acid derivative used is preferably an acid halide, imidazolide, anhydride or ester.

4. Reaction of a 2-cyanoaziridine of the general formula:

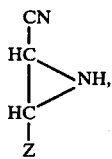
       (IX)

wherein Z has the same meaning as above, with a carbamoyl derivative of the general formula:

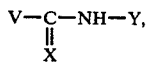
       (X)

wherein X and Y have the same meanings as above and V is an activating residue, the activating residue being, for example, a halogen atom. Otherwise, the reaction takes place under the same conditions as in process 1.

The conversion of compounds of general formula (I) into pharmacologically compatible salts can be carried out, for example, by reacting them with organic or inorganic bases, for example sodium methylate or sodium hydroxide.

The present invention also includes all stereoisomers of the compounds of general formula (I) which are formed due to the two asymmetrical carbon atoms, as well as to the nitrogen atoms.

The compounds of general formula (I) according to the present invention have strong immune-stimulating and cancerostatic properties. Furthermore, they stimulate the bone marrow, resulting in an increased formation of cells of the erythropoetic series and transmission of these cells into the peripheral blood stream. Therefore, the compounds (I) can be used not only for the treatment of bacterial and viral infections but also as cancerostatic agents.

For the preparation of pharmaceutical compositions, with immune-stimulating and cancerostatic action, at least one compound of general formula (I) and/or at least one salt thereof is mixed in the usual way with an appropriate solid or liquid pharmaceutical diluent or carrier and formed, for example, into tablets or dragees or, with the addition of appropriate adjuvants, suspended or dissolved in water or an oil, for example olive oil, and filled into capsules. Since the active materials are partially decomposed by gastric juices, the compositions intended for oral administration are preferably provided with a coating which only dissolves in the alkaline medium of the intestines or are mixed with appropriate carrier materials, for example high molecular weight fatty acids or carboxymethyl cellulose. Solid carrier materials which can be used include, for example, starch, lactose, mannitol, methyl cellulose, talc, highly dispersed silicic acid, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavoring and/or sweetening materials.

As injection medium, it is preferred to use water which contains the additives usual in the case of injection solutions, such as stabilizing agents, solubilizing agents, buffers and materials for regulating the osmotic pressure. Additives of this type include, for example, phosphate and carbonate buffers, ethanol, complex forming agents (such as ethylenediamine-tetraacetic acid and the nontoxic salts thereof), high molecular weight polymers (such as liquid polyethylene oxide) for viscosity regulation and sodium chloride, mannitol or the like for the regulation of the osmotic pressure.

Preferred compounds according to the present invention, apart from those mentioned in the following specific examples, include the following:

1-(N-trifluoroacetyl-carbamoyl)-2-cyanoaziridine
1-(N-cyclopentanecarbonyl-carbamoyl)-2-cyanoaziridine
1-(N-trifluoromethylsulphonyl-carbamoyl)-2-cyanoaziridine
1-(N-metylsulphonyl-thiocarbamoyl)-2-cyanoaziridine
1-(N-phenylsulphonyl-thiocarbamoyl)-2-cyanoaziridine
1-(N-cyanobenzoyl-carbamoyl)-2-cyanoaziridine
1-(N-cycloheptanecarbonyl-carbamoyl)-2-cyanoaziridine
1-(N-cyclooctanecarbonyl-carbamoyl)-2-cyanoaziridine
1-(N-cyclohexylsulphonyl-carbamoyl)-2-cyanoaziridine
1-[N-(thienyl-2-sulphonyl)-carbamoyl]-2-cyanoaziridine
1-(N-acetylglycyl-carbamoyl)-2-cyanoaziridine
1-(N-p-dimethylaminobenzoyl-carbamoyl)-2-cyanoaziridine
1-(N-m-sulphamoylbenzoyl-carbamoyl)-2-cyanoaziridine
1-(N-sulphamoyl-carbamoyl)-2-cyanoaziridine
1-(N-dimethylsulphamoyl-carbamoyl)-2-cyanoaziridine
1-(N-piperidinosulphonyl-carbamoyl)-2-cyanoaziridine 1-(N-morpholinosulphonyl-carbamoyl)-2-cyanoaziridine
1-(N-phenylsulphenyl-carbamoyl)-2-cyanoaziridine
1-(N-formyl-carbamoyl)-2-cyanoaziridine
1-(N-cyanocarbonyl-carbamoyl)-2-cyanoaziridine
Succinyl-bis-[1-(N-carbamoyl)-2-cyanoaziridine]
1-(N-α-naphthylacetyl-carbamoyl)-2-cyanoaziridine
1-(N-α-furylacetyl-carbamoyl)-2-cyanoaziridine
1-(N-α-thienylacetyl-carbamoyl)-2-cyanoaziridine
1-(N-p-chlorophenylacetyl-carbamoyl)-2-cyanoaziridine
1-(N-m-tolylacetyl-carbamoyl)-2-cyanoaziridine
1-(N-phthalimidoacetyl-carbamoyl)-2-cyanoaziridine
1-(N-3-m-nitrophenylacryloyl-carbamoyl)-2-cyanoaziridine
1-[N-(2-methylthiazole-5-carbonyl)-carbamoyl]-2-cyanoaziridine
1-[N-(5-nitro-1-methyl-2-imidazolecarbonyl)-carbamoyl]-2-cyanoaziridine
1-[N-(3-cyanopyridine-5-carbonyl)-carbamoyl]-2-cyanoaziridine
1-(N-3-α-furylacryloyl-carbamoyl)-2-cyanoaziridine
1-(N-diethylaminocarbonyl-carbamoyl)-2-cyanoaziridine
1-(N-phenylthioacetyl-carbamoyl)-2-cyanoaziridine
1-[N-(4-biphenylacetyl)-carbamoyl]-2-cyanoaziridine
1-[N-(quinoline-2-carbonyl)-carbamoyl]-2-cyanoaziridineterephthaloyl-bis-[1-(N-carbamoyl)-2-cyanoaziridine]
1-[N-(dimethoxyphosphoryloxyacetyl)-carbamoyl]-2-cyanoaziridine
1-(N-n-butylthioacetyl-carbamoyl)-2-cyanoaziridine
1-[N-(dimethylaminocarbonyloxyacetyl)-carbamoyl]-2-cyanoaziridine
1-(N-dimethoxyphosphonoacetyl-carbamoyl)-2-cyanoaziridine
1-(N-cyanoacetyl-carbamoyl)-2-cyanoaziridine
1-(N-dimethylaminoacetyl-carbamoyl)-2-cyanoaziridine
1-(N-p-methoxyphenylacetyl-carbamoyl)-2-cyanoaziridine
1-[N-(2-methylbenzthiazole-6-carbonyl)-carbamoyl]-2-cyanoaziridine
1-[N-(3-phenyl-5-methyl-isoxazole-4-carbonyl)-carbamoyl]-2-cyanoaziridine
bis-[1-(N-carbamoyl)-2-cyanoaziridine]-sulphone
1-[N-(piperidinocarbonyl)-carbamoyl]-2-cyanoaziridine
1-[N-(N-methyl-N-phenylaminocarbonyl)-carbamoyl]-2-cyanaziridine
1-(N-p-acetamidobenzoyl-carbamoyl)-2-cyanoaziridine
1-(N-dimethylaminooxalyl-carbamoyl)-2-cyanoaziridine
1-(N-diethylaminocarbonyloxyacetyl-carbamoyl)-2-cyanoaziridine
1-(N-p-methylthiophenylacetyl-carbamoyl)-2-cyanoaziridine
1-(N-succinimidoacetyl-carbamoyl)-2-cyanoaziridine
1-{N-[3-(5-nitro-2-furyl)-acryloyl]-carbamoyl}-2-cyanoaziridine
1-{N-[3-(5-methylsulphonyl-2-furyl)-acryloyl]-carbamoyl}-2-cyanoaziridine
1-[N-(2-chloropyridine-6-acetyl)-carbamoyl]-2-cyanoaziridine
1-[N-(5-methylsulphonyl-2-furyl)-carbamoyl]-2-cyanoaziridine
1-[N-(3-methoxy-pyridazine-6-carbonyl)-carbamoyl]-2-cyanoaziridine
1-(N-m-chlorophenylsulphenyl-carbamoyl)-2-cyanoaziridine
1-(n-p-methylphenylsulphenyl-carbamoyl)-2-cyanoaziridine
1-(N-p-nitrophenylsulphenyl-carbamoyl)-2-cyanoaziridine
1-(N-p-methylphenylsulphinyl-carbamoyl)-2-cyanoaziridine
1-[N-(2,3-dichlorothiophene-5-sulphonyl)-carbamoyl]-2-cyanoaziridine
1-[N-(4-ethoxycarbonylpyridine-6-sulphonyl)-carbamoyl]-2-cyanoaziridine
1-[N-(3-nitro-thiophene-5-sulphonyl)-carbamoyl]-2-cyanoaziridine
1-[N-(2-methyl-thiophene-5-sulphonyl)-carbamoyl]-2-cyanoaziridine
1-(N-ethylenedioxyphosphoryl-carbamoyl)-2-cyanoaziridine
1-[N-(3-methylthiopyridazine-6-carbonyl)-carbamoyl]-2-cyanoaziridine
1-[N-(p,N,N-diethylaminocarbonyl-benzoyl)-carbamoyl]-2-cyanoaziridine
1-(N-p-acetylbenzoyl-carbamoyl)-2-cyanoaziridine
1-(N-p-benzoylbenzoyl-carbamoyl)-2-cyanoaziridine
1-(N-p-acetoxyethylbenzoyl-carbamoyl)-2-cyanoaziridine
1-(N-p-methoxycarbonylethylbenzoyl-carbamoyl)-2-cyanoaziridine.

The following examples are given for the purpose of illustrating the present invention:

EXAMPLE 1

1-(N-Acetyl-carbamoyl)-2-cyanoaziridine.

1.76 g. 2-Cyanoaziridine is dissolved in 18 ml. anhydrous toluene and mixed dropwise, over the course of about 10 minutes, with a solution of 2.2 g. acetyl isocyanate in 8 ml. toluene, the addition being carried out at a temperature of from 20° to 30° C., while stirring. The reaction mixture is subsequently stirred for a further 30 minutes at ambient temperature and the precipitate formed is filtered off with suction, washed with toluene and then triturated with anhydrous diethyl ether. The crude material so obtained (3.6 g., m.p. 139°–142° C.) is dissolved in about 360 ml. ethyl acetate at 50° C., treated with active charcoal, filtered and the clear filtrate evaporated in vacuum. The evaporation residue obtained is triturated with anhydrous diethyl ether. There are thus obtained 2.9 g. 1-(N-acetyl-carbamoyl)-2-cyanoaziridine; m.p. 139°–142° C.

EXAMPLE 2

1-(N-Pivaloyl-carbamoyl)-2-cyanoaziridine.

A solution of 1.61 g. 2-cyanoaziridine in 30 ml. toluene is added dropwise at 20° to 30° C. to a solution of 3 g. trimethyl-acetyl isocyanate in 40 ml. anhydrous toluene and the reaction mixture then stirred for 1 hour at ambient temperature, whereafter the milky solution obtained is evaporated in a vacuum. The evaporation residue is rubbed with a glass rod until crystallization commences and the crystals obtained are triturated with diethyl ether. There is thus obtained 1.82 g. 1-(N-pivaloyl-carbamoyl)-2-cyanoaziridine which, after drying at 60° C. in a vacuum, melts at 136°–138° C.

EXAMPLE 3

1-(N-Chloroacetyl-carbamoyl)-2-cyanoaziridine.

A solution of 36 g. chloroacetyl isocyanate in 100 ml. toluene is added dropwise, while stirring and cooling, at a temperature of 20° to 30° C. to 20.4 g. 2-cyanoaziridine dissolved in 200 ml. toluene. The resulting suspension is further stirred for 1 hour at ambient temperature, then filtered with suction. The solid material obtained is washed with toluene and triturated with diethyl ether to give 62 g. of crude product. This is introduced into about 2.5 to 3 liters ethyl acetate at a temperature of 60° C., boiled for a short time and the clear solution treated with active charcoal. After filtration, the clear and still hot filtrate is evaporated in a vacuum and the evaporation residue is triturated with anhydrous diethyl ether and dried for 1 hour at 70° C. There are obtained 39.3 g. of product with a melting point of 152°–155° C. After further purification by stirring for 5 minutes with 200 ml. ethyl acetate at 60° C. and trituration of the crystals obtained with diethyl ether, there are obtained, after drying in a vacuum at 70° C. 28.9 g. 1-(N-chloroacetyl-carbamoyl)-2-cyanoaziridine; m.p. 152°–155° C.

EXAMPLE 4

1-(N-Dichloroacetyl-carbamoyl)-2-cyanoaziridine

A solution of 4.62 g. dichloroacetyl isocyanate in 10 ml. anhydrous toluene is added dropwise at a temperature of from 20° to 30° C. to a solution of 2 g. 2-cyanoaziridine in 20 ml. toluene. After stirring the reaction mixture for 30 minutes at ambient temperature, the resultant precipitate is filtered off with suction, washed with toluene and the filtered but still wet product is triturated with diethyl ether to give 5.3 g. of crude product. 6.3 g. of this product are dissolved in 300 ml. hot ethyl acetate, treated with active charcoal, boiled for a short time, suction filtered while still hot and the filtrate evaporated in a vacuum. The evaporation residue is triturated with diethyl ether to give 5 g. white 1-(N-dichloroacetyl-carbamoyl)-2cyanoaziridine; m.p. 164°–166° C.

EXAMPLE 5

1-(N-Trichloroacetyl-carbamoyl)-2-cyanoaziridine.

In a manner analogous to that described in Example 4, from 1.62 g. cyanoaziridine and 4.5 g. trichloroacetyl isocyanate, with stirring for 1 hour, there are obtained 2.82 g. 1-(N-trichloroacetyl-carbamoyl)-2-cyanoaziridine; m.p. 150°–152° C.

EXAMPLE 6

(a) 2-cyano-3-methylaziridine used as starting material can be prepared as follows: 160 g. bromine are added dropwise, while stirring at 25° C., over the course of 2 hours to 67 g. crotonitrile which, according to the NMR spectrum, contains about 40% of the trans form and about 60% of the cis form. The reaction mixture is then stirred for 1 hour at 30° C. and subsequently left to stand overnight at 25° C. The crude 2,3-dibromobutyronitrile thus obtained is used as such for the next step.

1-(N-Chloroacetyl-carbamoyl)-2-cyano-3-methylaziridine.

(b) In a manner analogous to that described in Example 4, there are obtained from 3.3 g. crude 2-cyano-3-methylaziridine (cis-trans mixture) in 30 ml. toluene and 4.8 g. chloroacetyl isocyanate in 15 ml. toluene, 4 g. white 1-(N-chloroacetyl-carbamoyl)-2-cyano-3-methylaziridine which, after drying at 60° C. in a vacuum, melts at 110°–120°–125° C. According to the NMR spectrum, there is obtained an isomeric mixture containing about 75% of the cis form and about 25% of the trans form.

A solution of 204.3 g. 2,3-dibromobutyronitrile in 200 ml. methanol is added dropwise, while stirring at 10°–15° C., to 630 ml. of an approximately 7 N methanolic solution of ammonia. The temperature of the reaction mixture is then allowed to rise to ambient temperature and then stirred at ambient temperature for 1 hour. 250 ml. Triethylamine are now allowed to run in, while stirring, followed by boiling for 3.5 hours under reflux, whereafter the solution is evaporated in a vacuum at bath temperature of 30° C. The evaporation residue is boiled up twice with 700 ml. amounts of diethyl ether, the triethylamine hydrobromide is filtered off with suction, the combined ethereal filtrates are treated with active charcoal, the charcoal is filtered off with suction and the filtrate is evaporated in a vacuum. The evaporation residue so obtained is dissolved in 600 ml. chloroform and the solution is shaken out with 150 ml. saturated aqueous sodium chloride solution. The organic phase is separated off, dried with anhydrous sodium sulphate, subsequently treated with charcoal, filtered and the clear filtrate obtained is evaporated in a vacuum at a bath temperature of 35° C. There are thus obtained 56.25 g. crude oily 2-cyano-3-methylaziridine.

EXAMPLE 7

1-(N-Benzoyl-carbamoyl)-2-cyanoaziridine.

A solution of 4.4 g. benzoyl isocyanate in 30 ml. toluene is added dropwise at 20° to 30° C. in the course of 10 minutes, while stirring, to 2.04 g. 2-cyanoaziridine dissolved in 60 ml. anhydrous toluene. The resultant reaction product is filtered off with suction, washed with toluene and the substance still moist from the filter is triturated with diethyl ether, 5.3 g. of crude product being obtained. This is now dissolved in 300 ml. hot benzene, a small amount of insoluble matter is filtered off with suction and the clear filtrate is cooled to bring about crystallization. After standing for 30 minutes, the crystals are filtered off with suction and washed with benzene and with diethyl ether to give 2.8 g. white 1-(N-benzoyl-carbamoyl)-2-cyanoaziridine; m.p. 144°–146° C. (after drying in a vacuum at 60° C.).

EXAMPLE 8

1-(N-4-Methylbenzoyl-carbamoyl)-2-cyanoaziridine.

In a manner analogous to that described in Example 7, from 2.04 g. 2-cyanoaziridine dissolved in 150 ml. toluene and a solution of 4.84 g. 4-methylbenzoyl isocyanate dissolved in 40 ml. toluene, there are obtained, after a reaction period of 1 hour at ambient temperature, 5 g. of crude product which melts at 177°–180° C. 0.5 g. of this material is boiled out with 30 ml. benzene, insoluble material is filtered off and the hot filtrate is left to crystallize. The crystals obtained are filtered off with suction and washed with benzene and diethyl ether to give 0.1 g. 1-(N-4-methylbenzoyl-carbamoyl)-2-cyanoaziridine; m.p. 178°–180° C.

EXAMPLE 9

1-(N-4-Chlorobenzoyl-carbamoyl)-2-cyanoaziridine.

In a manner analogous to that described in Example 7, from 2.04 g. 2-cyanoaziridine dissolved in 100 ml. toluene and a solution of 5.45 g. p-chlorobenzoyl isocyanate in 50 ml. toluene, there are obtained, after a reaction period of 1 hour at ambient temperature, 5.8 g. 1-(N-4-chlorobenzoyl-carbamoyl)-2-cyanoaziridine, which does not require any further purification; m.p. 160°–162° C.

EXAMPLE 10

1-(N-3-Nitrobenzoyl-carbamoyl)-2-cyanoaziridine.

A solution of 5.8 g. m-nitrobenzoyl isocyanate in 100 ml. toluene is added dropwise, while stirring, in the course of about 10 minutes to 2.04 g. 2-cyanoaziridine in 50 ml. anhydrous toluene. The reaction mixture is stirred for 30 minutes at ambient temperature and the precipitated solid product is filtered off with suction, washed with toluene and triturated with diethyl ether. There are thus obtained 4.8 g. white 1-(N-3-nitrobenzoyl-carbamoyl)-2-cyanoaziridine; m.p. 156°–158° C. (after drying for 1.5 hours in a vacuum at 70° C.).

EXAMPLE 11

1-(N-2,4-Dichlorobenzoyl-carbamoyl)-2-cyanoaziridine.

In a manner analogous to that described in Example 10, from 2.04 g. 2-cyanoaziridine dissolved in 50 ml. anhydrous toluene and a solution of 6.48 g. 2,4-dichlorobenzoyl isocyanate in 75 ml. toluene, there are obtained, after further stirring for 1 hour at ambient temperature, 4.7 g. 1-(N-2,4-dichlorobenzoyl-carbamoyl)-2-cyanoaziridine; m.p. 130°–132° C.

EXAMPLE 12

1-(N-2-Thiophene-carbonyl-carbamoyl)-2-cyanoaziridine.

(a) Thiophene-2-carbonyl isocyanate used as starting material is prepared in the following manner: 33.1 g. thiophene-2-carboxylic acid amide (m.p. 179°–180° C.) are boiled under reflux for 6 hours with 38 g. oxalyl chloride in 105 ml. ethylene chloride. The reaction mixture is then evaporated in a vacuum and the residue is fractionated. 33.4 g. thiophene-2-carbonyl isocyanate are obtained at 98°–100° C./12 mm.Hg.

(b) 2.76 g. Thiophene-2-carbonyl isocyanate are dissolved in 45 ml. anhydrous toluene and mixed dropwise, while stirring, at 20° to 30° C. with a solution of 1.22 g. 2-cyanoaziridine in 30 ml. toluene. Stirring is continued for 1 hour at ambient temperature and the precipitate obtained is filtered off with suction, washed with toluene and subsequently triturated with diethyl ether. There are thus obtained 3.4 g. 1-(N-2-thiophene-carbonyl-carbamoyl)-2-cyanoaziridine; m.p. 156°–160° C., which still contains a little thiophene-2-carboxylic acid amide.

EXAMPLE 13

1-[N-(1-Methyl-3-nitro-4-pyrazolylcarbonyl)-carbamoyl]2-cyanoaziridine.

(a) 1-Methyl-3-nitropyrazole-4-carbonyl isocyanate used as starting material is prepared as follows: 10.2 g. 1-methyl-3-nitro-4-pyrazole-carboxamide (m.p. 190°–192° C.) are boiled under reflux for 5 hours with 24 ml. oxalyl chloride in 120 ml. chlorobenzene (b.p. 132° C.), whereafter the solvent is evaporated off in a vacuum and the oily residue left to crystallize 11.6 g. crude 1-methyl-3-nitropyrazole-4-carbonyl isocyanate being obtained; m.p. 55°–59° C.

(b) 2.8 g. Crude 1-methyl-3-nitropyrazole-4-carbonyl isocyanate (m.p. 55°–59° C.) are dissolved in 100 ml. anhydrous diethyl ether, a little insoluble material is separated off, 0.86 g. 2-cyanoaziridine in 20 ml. anhydrous diethyl ether is slowly added thereto and the resulting suspension is subsequently stirred for 1 hour at ambient temperature. The crystals formed are filtered off with suction and triturated with anhydrous diethyl ether to give 1.8 g. 1-[N-(1-methyl-3-nitro-4-pyrazolyl-carbonyl)carbamoyl]-2-cyanoaziridine; m.p. 58°–64° C. The product is hygroscopic and contains a little 1-methyl-3-nitropyrazole-4-carboxamide.

EXAMPLE 14

1-(N-Ethoxycarbonyl-carbamoyl)-2-cyanoaziridine.

A solution of 1.9 g. ethoxycarbonyl isocyanate in 40 ml. toluene is added dropwise, while stirring, at 20°–30° C. to 1.12 g. 2-cyanoaziridine in 30 ml. anhydrous toluene. The reaction mixture is further stirred for 1 hour at ambient temperature and the resultant precipitate is filtered off with suction, washed with toluene and triturated with diethyl ether to give 1.85 g. 1-(N-ethoxycarbonyl-carbamoyl)-2-cyanoaziridine; m.p. 108°–110° C.

EXAMPLE 15

1-(N-Chloroacetyl-carbamoyl)-2-cyano-3-phenyl-aziridine.

(a) 2-Cyano-3-phenyl-aziridine used as starting material is prepared as follows: from cinnamic acid nitrile and bromine there is prepared, in the manner described in the literature, 3-phenyl-2,3-dibromopropionitrile and this is used in the form of the crude product (m.p. 80°–90° C.). 5.1 g. of this dibromo compound are introduced into a solution of ammonia in 31 ml. dimethyl sulphoxide. Gaseous ammonia is then passed into the solution for 1 hour, whereafter the solution is mixed with 120 ml. water and extracted 4 times with 120 ml. amounts of diethyl ether. After evaporation of the combined ethereal extracts in a vacuum, there are obtained 2.63 g. crude 2-cyano-3-phenyl-aziridine, 0.5 g. thereof give, after trituration with about 1 ml. diethyl ether, 0.12 g. of crystals; m.p. 97°–100° C.

(b) 1 g. Crude 2-cyano-3-phenyl-aziridine is dissolved in 25 ml. anhydrous diethyl ether. A solution of 0.83 g. chloroacetyl isocyanate in 3.5 ml. diethyl ether is added thereto dropwise, while stirring, and the reaction mixture is further stirred for 1 hour at ambient temperature. The precipitate obtained is then filtered off with suction, washed with diethyl ether and dried in a vacuum. There is thus obtained 1.24 g. 1-(N-chloroacetyl-carbamoyl)-2-cyano3-phenyl-aziridine; m.p. 153°–158°–165° C. According to the NMR spectrum, the product is an isomeric mixture containing about 30% of the trans form and about 70% of the cis form.

EXAMPLE 16

1-(N-Trifluoromethylsulphenyl-carbamoyl)-2-cyanoaziridine.

3.5 g. Trifluoromethylsulphenyl isocyanate are dissolved in 35 ml. toluene and a solution of 1.67 g. 2-cyanoaziridine in 25 ml. toluene added dropwise thereto, while stirring, at a temperature between 20° and 30° C. The reaction mixture is further stirred for 1 hour at ambient temperature, the inner wall of the reaction vessel used is scratched with a glass rod and the resultant crystalline suspension is further stirred for 1 hour at ambient temperature. The crystals are now filtered off with suction and washed with toluene and the crystals are triturated with petroleum ether to give 2.4 g. 1-(N-trifluoromethylsulphenyl-carbamoyl)-2-cyanoaziridine; m.p. 83°–85° C.

EXAMPLE 17

1-(N-Mesyl-carbamoyl)-2-cyanoaziridine.

1.6 g. 2-Cyanoaziridine are dissolved in 16 ml. anhydrous diethyl ether. This solution is mixed dropwise, while cooling with ice, with an anhydrous ethereal solution of 2.6 g. mesyl isocyanate. After further stirring for 30 minutes at ambient temperature, the precipitated crystals are filtered off with suction, washed with diethyl ether and dried in a vacuum. There are obtained 2.9 g. (65% of theory) of 1-(N-mesyl-carbamoyl)-2-cyanoaziridine in the form of white crystals; m.p. 110°–112° C.

EXAMPLE 18

1-(N-4-Methylbenzenesulphonyl-carbamoyl)-2-cyanoaziridine.

A solution of 0.408 g. 2-cyanoaziridine in 10 ml. toluene is added dropwise, while stirring, at a temperature of 20° to 30° C. to a solution of 1.18 g. p-toluene-sulphonyl isocyanate in 15 ml. anhydrous toluene. The flask containing the reaction mixture is scratched with a glass rod and the crystal suspension which thereby results is further stirred for 1 hour at ambient temperature, filtered off with suction, washed with toluene and the crystals obtained triturated with diethyl ether. There is obtained 1.1 g. 1-(N-4-methylbenzenesulphonyl-carbamoyl)-2-cyanoaziridine; m.p. 156°–158° C.

EXAMPLE 19

1-(N-p-Methoxyphenylsulphonyl-carbamoyl)-2-cyanoaziridine.

2.5 g. 2-Cyanoaziridine are dissolved in 25 ml. anhydrous diethyl ether. To this solution, in an ice-bath, there is added dropwise a solution of 7.15 g. p-methoxyphenylsulphonyl isocyanate in 50 ml. anhydrous diethyl ether. After completion of the separating out of the crystals, they are filtered off with suction, washed with diethyl ether and dried in a vacuum. There are obtained 8.05 g. (85% of theory) 1-(N-p-methoxybenzenesulphonyl-carbamoyl)-2-cyanoaziridine in the form of white crystals; m.p. 125°–129° C. (bubble formation).

For the preparation of a water-soluble sodium salt, 0.281 g. of the compound obtained is dissolved in 5 ml. methanol, mixed with 0.054 g. sodium methylate and the solution evaporated in a vacuum. After stirring the residue with anhydrous diethyl ether, there are obtained 0.2 g. of the sodium salt in the form of white crystals; m.p. 197°–200° C. (decomp.).

EXAMPLE 20

1-(N-o-Tolylsulphonyl-carbamoyl)-2-cyanoaziridine.

1.8 g. 2-Cyanoaziridine are dissolved in 18 ml. anhydrous diethyl ether. To this solution there is added dropwise, in an ice-bath, a solution of 4.8 g. o-tolyl sulphonyl isocyanate in 48 ml. anhydrous diethyl ether. After further stirring the reaction mixture for 1 hour at ambient temperature, the precipitated crystals are filtered off with suction, washed with diethyl ether and dried in a vacuum. There are thus obtained 5.05 g. (78% of theory) of white crystals which, for further purification, are dissolved in a warm mixture of diethyl ether and ethyl acetate. The filtrate is mixed with ligroin until turbidity appears and then cooled. There are thus obtained white crystals of 1-(N-o-tolylsulphonyl-carbamoyl)-2-cyanoaziridine; m.p. 125°–129° C. (bubble formation).

In a manner analogous to that described in Example 19, there is obtained from the product a water-soluble sodium salt; m.p. 89°–93° C. (decomp.).

EXAMPLE 21

1-(N-p-Chlorophenylsulphonyl-carbamoyl)-2-cyanoaziridine.

3.2 g. 2-Cyanoaziridine are reacted with 9.2 g. p-chlorophenylsulphonyl isocyanate in a manner analogous to that described in Example 20 to give 8.3 g. (69% of theory) 1-(N-p-chlorophenylsulphonyl-carbamoyl)-2-cyanoaziridine in the form of white crystals; m.p. 122°–126° C. (bubble formation).

In a manner analogous to that described in Example 19, there is obtained from the product a water-soluble sodium salt; m.p. 175°–179° C. (decomp.).

EXAMPLE 22

1-(N-Ethoxycarbonyl-thiocarbamoyl)-2-cyanoaziridine.

3.94 g. Ethoxycarbonyl isothiocyanate are dissolved in 75 ml. anhydrous toluene and to this there is added dropwise, at a temperature between 20° and 30° C., a solution of 2.04 g. 2-cyanoaziridine in 50 ml. toluene. The reaction mixture is stirred at ambient temperature for a further hour and the crystals obtained are filtered off with suction, washed with toluene and then triturated with diethyl ether. There are thus obtained 4 g. 1-(N-ethoxycarbonyl-thiocarbamoyl)-2-cyanoaziridine; m.p. 152°–155° C. (foaming up).

EXAMPLE 23

1-(N-Benzoyl-thiocarbamoyl)-2-cyanoaziridine.

A solution of 2.04 g. 2-cyanoaziridine in 75 ml. anhydrous diethyl ether is added dropwise to a solution of 4.9 g. benzoyl isothiocyanate in 75 ml. anhydrous diethyl ether. The reaction mixture is further stirred for 1 hour at ambient temperature and the crystals obtained are filtered off with suction and triturated with anhydrous diethyl ether to give 2.7 g. 1-(N-benzoylthiocarbamoyl)-2-cyanoaziridine; m.p. 135°–140° C. (foaming up).

EXAMPLE 24

1-(N-Ethanesulphonyl-carbamoyl)-2-cyanoaziridine.

1.4 g. 2-Cyanoaziridine is dissolved in 14 ml. anhydrous diethyl ether. While cooling with ice, to this solution there is added dropwise a solution of 3 g. ethanesulphonyl isocyanate in 30 ml. anhydrous diethyl ether. The reaction mixture is further stirred for 30 minutes at ambient temperature and the precipitated crystals are filtered off with suction. After washing with diethyl ether and drying in a vacuum, there are obtained 1.7 g. (41% of theory) 1-(N-ethanesulphonylcarbamoyl)-2-cyanoaziridine in the form of white crystals; m.p. 70°-73° C. (bubble formation).

EXAMPLE 25

1-(N-Ethoxalyl-carbamoyl)-2-cyanoaziridine.

A solution of 2.04 g. 2-cyanoaziridine in 50 ml. anhydrous toluene is added dropwise, while stirring, at a temperature between 20° and 30° C. to a solution of 4.3 g. carbethoxy-carbonyl isocyanate in 50 ml. anhydrous toluene, a colorless oil separating out which crstallizes after rubbing with a glass rod. The resultant crystal suspension is further stirred for 1 hour at ambient temperature, then filtered off with suction and washed with toluene and the crystals are triturated with diethyl ether. There are obtained 4.9 g. 1-(N-ethoxalyl-carbamoyl)-2-cyanoaziridine; m.p. 104°-106° C.

EXAMPLE 26

1-(N-Phenylsulphonyl-carbamoyl)-2-cyanoaziridine.

0.82 g. 2-Cyanoaziridine are dissolved in 8 ml. toluene and, while cooling with ice, 2 g. phenylsulphonyl isocyanate, dissolved in 10 ml. toluene, are added dropwise thereto. After further stirring the reaction mixture for 45 minutes at ambient temperature, the precipitated crystals are filtered off with suction, washed with diethyl ether and dried in a vacuum. There is thus obtained 1.45 g. (53% of theory) 1-(N-phenylsulphonyl-carbamoyl)2-cyanoaziridine in the form of white crystals; m.p. 103°-108° C.

EXAMPLE 27

1-(N-m-Nitrophenylsulphonyl-carbamoyl)-2-cyanoaziridine.

A solution of 4 g. m-nitrophenylsulphonyl isocyanate in a mixture of 40 ml. anhydrous diethyl ether and 30 ml. toluene is added dropwise to a solution of 1.3 g. 2-cyanoaziridine in 13 ml. anhydrous diethyl ether. Stirring is continued at ambient temperature until crystal separation is complete, whereafter the crystals are filtered off with suction and washed with diethyl ether. There are obtained 2.5 g. (48% of theory) 1-(N-m-nitrophenylsulphonylcarbamoyl)-2-cyanoaziridine; m.p. 100°-103° C.

EXAMPLE 28

1-(N-Acryloyl-carbamoyl)-2-cyanoaziridine.

A solution of 1.6 g. crude acrylic isocyanate in 30 ml. toluene is mixed at 20°-30° C. with a solution of 1.12 g. 2-cyanoaziridine in 10 ml. toluene. The reaction mixture is further stirred for 1 hour at ambient temperature and the precipitated crystalline substance is filtered off with suction, washed with toluene and triturated with anhydrous diethyl ether to give 2.06 g. 1-(N-acryloyl-carbamoyl)-2-cyanoaziridine; m.p. 158°-160° C. The product is practically insoluble in water but goes into solution upon the addition of an excess of 2 N aqueous sodium hydroxide solution.

EXAMPLE 29

1-(N-Cinnamoyl-carbamoyl)-2-cyanoaziridine.

A solution of 0.98 g. 2-cyanoaziridine in 20 ml. toluene is added dropwise, while stirring, at 20° to 30° C. to 2.5 g. cinnamoyl isocyanate dissolved in 20 ml. toluene. The resultant suspension is stirred for 1 hour at ambient temperature, then filtered off with suction and washed with toluene. The crystals obtained are triturated with anhydrous diethyl ether and dried for 1 hour at 50° C. in a vacuum to give 1.9 g. of crude product; m.p. 134°-136° C. This crude product is boiled with 50 ml. ethyl acetate for a short time, mixed with active charcoal and then filtered. The hot ethyl acetate filtrate is evaporated in a vacuum and the evaporation residue triturated with anhydrous diethyl ether. There is thus obtained 1.2 g. 1-(N-cinnamoyl-carbamoyl)-2-cyanoaziridine; m.p. 163°-164° C. The compound is practically insoluble in water but goes into solution upon the addition of excess 2 N aqueous sodium hydroxide solution.

EXAMPLE 30

1-(N-Ethoxycarbonylacetyl-carbamoyl)-2-cyanoaziridine.

(a) Ethoxycarbonylacetyl isocyanate used as starting material is prepared as follows: 26.2 g. carbethoxyacetamide (m.p. 46°-50° C.), 80 ml. ethylene chloride and 25 g. oxalyl chloride are boiled under reflux for 6 hours. The ethylene chloride is then evaporated off in a vacuum and the solid evaporation residue is distilled in a vacuum; b.p. 66° C./0.1 mm.Hg; at this temperature, 8.2 g. distillate of ethoxycarbonylacetyl isocyanate are obtained.

(b) 4 g. Ethoxycarbonylacetyl isocyanate are dissolved in 40 ml. toluene and mixed, while stirring, at 20°-30° C. with a solution of 1.73 g. 2-cyanoaziridine in 20 ml. toluene. After about 5 minutes, an oily deposit separates out which, after trituration, gradually solidifies. The suspension thus obtained is further stirred for 1 hour at ambient temperature, then filtered off with suction and washed with toluene and the solid product triturated with anhydrous diethyl ether. There are thus obtained 3.7 g. 1-(N-ethoxycarbonylacetyl-carbamoyl)-2-cyanoaziridine; m.p. 121°-123° C. The product is practically insoluble in water but is soluble in dilute aqueous sodium hydroxide solution.

EXAMPLE 31

1-(N-Methylsulphonylacetyl-carbamoyl)-2-cyanoaziridine.

(a) Methylsulphonylacetyl isocyanate used as starting material is prepared as follows: 16.44 g. methylsulphonylacetamide (m.p. 113°-114° C.) are suspended in 60 ml. ethylene chloride. 11.6 g. Oxalyl chloride are slowly added thereto and the reaction mixture is boiled under reflux. The ethylene chloride is then distilled off from the solution obtained to give 16.7 g. of crude methylsulphonylacetyl isocyanate.

(b) 6.52 g. Crude methylsulphonylacetyl isocyanate are dissolved in 60 ml toulene and undissolved oil in separated off. A solution of 1.36 g. 2-cyanoaziridine in 20 ml. toulene is added, while stirring, at 20° to 30° C. to this solution, whereafter the reaction mixture is stirred at ambient temperature for 1 hour. The semi-solid substance obtained is triturated with fresh toluene and the solid substance so obtained is filtered off with suction and triturated with anhydrous diethyl ether to give 1.4 g. 1-(N-methylsulphonylacetyl-carbamoyl)-2-cyanoaziridine; m.p. 126°-128° C. This compound is practically insoluble in water but dissolves in dilute aqueous sodium hydroxide solution.

EXAMPLE 32

1-(N-p-Ethoxycarbonylbenzoyl-carbamoyl)-2-cyanoaziridine.

(a) 4-Ethoxycarbonylbenzoyl isocyanate used as starting material is prepared as follows: 9.7 g. crude 4-ethoxycarbonylbenzoic acid (m.p. 168°-170° C.) are boiled under reflux with 40 g. thionyl chloride and 0.2 ml. triethylamine for 3 hours, a clear solution being obtained after about 30 minutes. Excess thionyl chloride is then evaporated off and the oily evaporation residue is dissolved in 20 ml. dioxane. This solution is added dropwise to 200 ml. concentrated aqueous ammonia solution at 0° to 10° C. and then further stirred at this temperature for 30 minutes. The solid product is filtered off with suction and washed with ice water to give 9.5 g. crude 4-ethoxycarbonylbenzamide; m.p. 176°-178° C.

The 9.5 g. of the amide thus obtained are boiled under reflux for 6 hours with 20 ml. ethylene chloride and 7.3 g. oxalyl chloride. The ethylene chloride is then evaporated off in a vacuum to give 9.85 g. of an oily residue, which is crude 4-ethoxycarbonylbenzoyl isocyanate.

(b) A solution of 0.34 g. 2-cyanoaziridine in 10 ml. toluene is added dropwise, while stirring, at 20° to 30° C. to 1.1 g. crude 4-ethoxycarbonylbenzoyl isocyanate dissolved in 10 ml. toluene. The reaction mixture is further stirred for 1 hour at ambient temperature, during the course of which a further 10 ml. toluene are added thereto in order to keep the resultant slurry stirrable. The reaction mixture is then filtered with suction and the solid product is washed with toluene and triturated with anhydrous diethyl ether to give 1.1 g. 1-(N-p-ethoxycarbonylbenzoyl-carbamoyl)-2-cyanoaziridine (m.p. 146°-148° C.) which still contains a little 1-(N-p-methoxycarbonylbenzoyl-carbamoyl)-2-cyanoaziridine. The product obtained is practically insoluble in water but is soluble in dilute aqueous sodium hydroxide solution.

EXAMPLE 33

1-(N-Cyclohexanecarbonyl-carbamoyl)-2-cyanoaziridine

A solution of 1.41 g. 2-cyanoaziridine in 20 ml. toluene is added dropwise, while stirring, at 20°-30° C. to a solution of 3.2 g. cyclohexanecarbonyl isocyanate in 50 ml. toluene. The reaction mixture is further stirred for 15 minutes at ambient temperature and a certain amount of greasy material which precipitates out is separated off. The clear solution is further stirred for 1 hour at ambient temperature and the crystals which have, in the meantime separated out, are filtered off with suction. They are washed with toluene, triturated with anhydrous diethyl ether and dried in a vacuum for 1 hour at 50° C. There are thus obtained 3.2 g. 1-(N-cyclohexanecarbonyl-carbamoyl)-2-cyanoaziridine; m.p. 142°-144° C. This compound is practically insoluble in water but dissolves in dilute aqueous sodium hydroxide solution.

EXAMPLE 34

1-(N-n-Butylsulphonyl-carbamoyl)-2-cyanoaziridine 1.5 g. 2-Cyanoaziridine are dissolved in 15 ml. anhydrous diethyl ether and mixed dropwise, while stirring and cooling with ice, with a solution of 4 g. n-butylsulphonyl isocyanate in 40 ml. anhydrous diethyl ether. After further stirring for 1 hour at ambient temperature, the clear solution is evaporated and the oily residue caused to crystallize with diethyl ether-ligroin. The crystals are filtered off with suction and washed with diethyl ether-ligroin. There are obtained 2.0 g. (40% of theory) 1-(N-n-butylsulphonyl-carbamoyl)-2-cyanoaziridine; m.p. 80°-85° C.

EXAMPLE 35

1-(N-p-Methoxybenzoyl-carbamoyl)-2-cyanoaziridine

In a manner analogous to that described in Example 1, from 2.04 g. 2-cyanoaziridine, dissolved in 50 ml. toluene, and a solution of 5.35 g. p-methoxybenzoyl isocynate in 75 ml. toluene and further stirring for 1 hour at ambient temperature, there are obtained 3.5 g. 1-(N-p-methoxybenzoyl-carbamoyl)-2-cyanoaziridine; m.p. 130°-132° C., without purification with ethyl acetate.

EXAMPLE 36

1-(N-n-Pentanecarbonyl-carbamoyl)-2-cyanoaziridine (a) n-Pentanecarbonyl isocyanate used as starting material is obtained by boiling under reflux for 6 hours 12 g. capronamide (m.p. 99°-101° C.) and 8.1 ml. oxalyl chloride in 42 ml. ethylene chloride, distilling off the solvent and fractionating the residue. The yield of n-pentanecarbonyl isocyanate is 5.5 g.; b.p. 60°-63° C./17 mm.Hg.

(b) In a manner analogous to that described in Example 14, from 0.81 g. 2-cyanoaziridine, dissolved in 8 ml. toluene, and a solution of 1.7 g. n-pentanecarbonyl isocyanate in 17 ml. toluene, there are obtained, without purification with diethyl ether, 1.6 g. 1-(N-n-pentanecarbonyl-carbamoyl)-1-cyanoaziridine; m.p. 143°-144° C.

EXAMPLE 37

N,N'-Bis-(1-carbanoyl-2-cyanoaziridinyl)-sulphanilamide 3 g. 4-Isocyanatophenylsulphonyl isocyanate are dissolved in 100 ml. anhydrous diethyl ether and a solution of 2 g. 2-cyanoaziridine in 100 ml. anhydrous diethyl ether added dropwise thereto at 5° C. After stirring the reaction mixture for 2 hours, the precipitated crystals are filtered off with suction, washed with diethyl ether and dried in a vacuum. There are obtained 3.9 g. N,N'-bis-(1-carbonyl-2-cyanoaziridinyl)-sulphanilamide; m.p. 97° C. (decomp.).

EXAMPLE 38

1-(N-Phenoxyacetyl-carbamoyl)-2-cyanoaziridine 1.26 g. 2-Cyanoaziridine are dissolved in 20 ml. toluene and, while stirring at 20°-30° C., a solution of 3.3 g. phenoxyacetyl isocyanate in 40 ml. toluene is added thereto, while stirring. After further stirring for 1 hour at ambient temperature, the precipitated material is filtered off with suction and washed with toluene and the reaction product is triturated with anhydrous diethyl ether. After drying, there are obtained 3.6 g. 1-(N-phenoxyacetyl-carbamoyl)-2-cyanoaziridine; m.p. 134°-136° C.

EXAMPLE 39

1-(N-p-Chlorophenoxyacetyl-carbamoyl)-2-cyanoaziridine (a) p-Chlorophenoxyacetyl isocyanate used as starting material is prepared as follows: 3.72 g. p-chlorophenoxyacetamide (139°–140° C.) are suspended in 35 ml. ethylene chloride. 2.1 ml. Oxalyl chloride are added dropwise thereto, whereafter the reaction mixture is heated under reflux for 6 hours. Excess oxalyl chloride is then distilled off and the residue is fractionated in a vacuum. At a boiling point of 120° C./0.01 mm.Hg, there are obtained 2.73 g. p-chlorophenoxyacetyl isocyanate.

(b) 0.7 g. 2-Cyanoaziridine are dissolved in 5 ml. diethyl ether and this solution is added dropwise, while stirring, to a solution of 1.85 g. p-chlorophenoxyacetyl isocyanate in 5 ml. diethyl ether at ambient temperature. After stirring the reaction mixture for 1 hour, the precipitated reaction product is filtered off with suction and then washed with anhydrous diethyl ether. After drying, there are obtained 2.1 g. 1-(N-p-chlorophenoxyacetyl-carbamoyl)-2-cyanoaziridine; m.p. 152°–155° C. This product is practically insoluble in water but dissolves in dilute aqueous sodium hydroxide solution.

EXAMPLE 40

1-(N-Cyclohexylacetyl-carbamoyl)-2-cyanoaziridine (a) Cyclohexylacetyl isocyanate used as starting material is prepared as follows: 14.1 g. cyclohexylacetamide in 40 ml. ethylene chloride are carefully mixed with 14.5 g. oxalyl chloride and the reaction mixture boiled under reflux for 3 hours. Excess oxalyl chloride is distilled off in a vacuum and the evaporation residue fractionated in a vacuum, 11.6 g. cyclohexylacetyl isocyanate being obtained; b.p. 48°–50° C./0.5 mm.Hg.

(b) 1.14 g. 2-cyanoaziridine are dissolved in 14 ml. toluene and, while stirring at ambient temperature, a solution of 2.8 g. cyclohexylacetyl isocyanate in 30 ml. toluene added thereto. The reaction mixture is then stirred for 1 hour and the precipitated material is filtered off with suction, washed with toluene and finally triturated with diethyl ether to give 2.8 g. 1-(N-cyclohexylacetyl-carbamoyl)-2-cyanoaziridine; m.p. 142°–144° C. The product is practically insoluble in water but is soluble in dilute aqueous sodium hydroxide solution. It is contaminated with a small amount of chlorine-containing substance.

EXAMPLE 41

1-(N-Dodecanoyl-carbamoyl)-2-cyanoaziridine (a) Dodecanoyl isocyanate used as starting material is prepared as follows: 19.9 g. lauric acid amide (m.p. 104°–105° C.) are suspended in 40 ml. ethylene chloride. 14.5 g. Oxalyl chloride are added portionwise thereto at 0° C. and the reaction mixture is slowly heated under reflux, a clear solution being obtained after 2 hours. Boiling under reflux is continued for a total of 6 hours. The reaction mixture is left to cool overnight and the suspension obtained is evaporated in a vacuum. There ae thus obtained 23.5 g. of evaporation residue. 21 g. of this are fractionated in a vacuum. At a boiling point of 98°–101° C./0.05 mm.Hg, there are obtained 6.1 g. dodecanoyl isocyanate, which is very hygroscopic.

(b) A solution of 1 g. 2-cyanoaziridine in 10 ml. toluene is introduced, while stirring and at a temperature below 25° C., into a solution of 3.3 g. dodecanoyl isocyanate in 40 ml. toluene. The reaction mixture is then stirred for 1 hour at ambient temperature and the material which separates out is filtered off with suction and washed with toluene. The reaction product obtained is triturated with diethyl ether to give 2.2 g. 1-(N-dodecanoyl-carbamoyl)-2-cyanoaziridine; m.p. 140°–143° C.

EXAMPLE 42

1-(N-$\beta$-Naphthalene-carbonyl-carbamoyl)-2-cyanoaziridine (a) Naphthalene-2-carbonyl-isocyanate used as starting material is prepared as follows: 17.1 g. naphthalene-2-carboxamide (m.p. 190°–192° C.) is boiled under reflux for 6 hours in 40 ml. ethylene chloride with 14.5 g. oxalyl chloride, a clear solution being formed after 2 hours. Excess solvent is now distilled off and the solid evaporation residue is fractionated in a vacuum. At a boiling point of 120°–122° C./0.03 mm.Hg, there are obtained 7.8 g. naphthalene-2-carbonyl isocyanate.

(b) 0.68 g. 2-Cyanoaziridine in 10 ml. toluene are introduced, while stirring at 25° C., into a solution of 1.97 g. naphthalene-2-carbonyl isocyanate in 40 ml. toluene. The reaction mixture is further stirred for 1 hour and the precipitated material is filtered off with suction, washed with toluene and triturated with anhydrous diethyl ether to give 1.9 g. 1-(N-$\beta$-naphthalene-carbonyl-carbamoyl)-2-cyanoaziridine; m.p. 164°–166° C.

EXAMPLE 43

1-[N-(5,6,7,8-Tetrahydronaphthalene-2-carbonyl)-carbamoyl]-2-cyanoaziridine (a) The 5,6,7,8-Tetrahydronaphthalene-2-carbonyl isocyanate used as starting material is prepared as follows: 3.8 g. 5,6,7,8-tetrahydronaphthalene-2-carboxylic acid are boiled under reflux for 2 hours with 11.5 g. thionyl chloride. The solution is then evaporated in a vacuum and the oily residue is fractionated in a vacuum. At a boiling point of 108°–110° C./0.03 mm.Hg, there are obtained 3 g. of the corresponding carboxylic acid chloride. This is dissolved in 30 ml. anhydrous diethyl ether, ammonia gas is passed in for 45 minutes, while stirring, and the precipitated material is filtered off with suction, washed with diethyl ether and triturated with water. There are thus obtained 2.2 g. 5,6,7,8-tetrahydronaphthalene-2-carboxamide; m.p. 139°–141° C. This substance is boiled under reflux for 2 hours in 5 ml. ethylene chloride with 1.9 g. oxalyl chloride (suspended) and then the clear solution obtained is boiled for a further 2 hours. The reaction mixture is then evaporated in a vacuum and the oily residue obtained is fractionated in a vacuum. At a boiling point of 118°–120° C./0.05 mm.Hg, there is obtained 1.2 g. 5,6,7,8-tetrahydronaphthalene-2-carbonyl isocyanate.

(b) 0.41 g. 2-Cyanoaziridine are dissolved in 10 ml. toluene and added at ambient temperature to a solution of 1.2 g. 5,6,7,8-tetrahydronaphthalene-2-carbonyl isocyanate in 20 ml. toluene. The reaction mixture is further stirred for 1 hour and the precipitated substance is filtered off with suction, washed with toluene and triturated with anhydrous diethyl ether to give 0.9 g. 1-[N-(5,6,7,8-tetrahydronaphthalene-2-carbonyl)-carbamoyl]-2-cyanoaziridine; m.p. 166°–168° C. This compound is practically insoluble in water but is soluble in dilute aqueous sodium hydroxide solution.

EXAMPLE 44

1-(N-2-Furoyl-carbamoyl)-2-cyanoaziridine

A solution of 0.7 g. 2-cyanoaziridine in 3 ml. anhydrous diethyl ether is introduced at ambient temperature, while stirring, into a solution of 1.37 g. 2-furoyl isocyanate in 7 ml. anhydrous diethyl ether. The reaction mixture is further stirred for 1 hour and the precipitated material (2.22 g.) is filtered off with suction, triturated with about 10 ml. anhydrous diethyl ether and filtered off with suction to give 1.6 g. 1-(N-2-furoyl-carbamoyl)-2-cyanoaziridine; m.p. 148°–150° C. This compound is practically insoluble in water but dissolves in dilute aqueous sodium hydroxide solution.

EXAMPLE 45

1-(N-2-Benzofuroyl-carbamoyl)-2-cyanoaziridine (a) 2-Benzofuroyl isocyanate used as starting material is prepared by boiling under reflux for 3 hours 12.2 g. benzofuran-2-carboxamide in 40 ml. ethylene chloride with 14.5 g. oxalyl chloride, evaporating off excess oxalyl chloride in a vacuum and fractionating the solid evaporation residue in a vacuum. At a boiling point of 102°–104° C./0.03 mm.Hg, there are obtained 9.48 g. 2-benzofuroyl isocyanate.

(b) A solution of 1.36 g. 2-cyanoaziridine in 15 ml. toluene is introduced at ambient temperature, while stirring, into a solution of 3.74 g. 2-benzofuroyl isocyanate in 60 ml. toluene. The reaction mixture is further stirred for 1 hour and the precipitated substance is filtered off with suction, washed with toluene and triturated with anhydrous diethyl ether to give 3.3 g. 1-(N-2-benzofuroyl-carbamoyl)-2-cyanoaziridine; m.p. 190°–192° C. This compound is practically insoluble in water but dissolves in dilute aqueous sodium hydroxide solution.

EXAMPLE 46

1-(N-3,4-Methylenedioxybenzoyl-carbamoyl)-2-cyanoaziridine (a) 3,4-Methylenedioxybenzoyl isocyanate used as starting material is prepared by boiling under reflux for 3 hours 1.65 g. 3,4-methylenedioxybenzamide (m.p. 165°–167° C.) and 15 ml. oxalyl chloride, distilling off excess oxalyl chloride and fractionating the solid evaporation residue in a vacuum at about 0.03 mm.Hg. There is thus obtained 0.98 g. of solid, very hygroscopic 3,4-methylenedioxybenzoyl isocyanate.

(b) 0.26 g. 2-Cyanoaziridine are dissolved in 5 ml. toluene and introduced, while stirring at 0° C., into a solution of 0.73 g. 3,4-methylenedioxybenzoyl isocyanate in 25 ml. toluene. The reaction mixture is further stirred for 1 hour at 0° C. and the precipitated material (0.65 g.) is filtered off with suction at ambient temperature and briefly boiled with isopropanol, 0.2 g. of the desired 1-(N-3,4-methylenedioxybenzoyl-carbamoyl)-2-cyanoaziridine thereby remaining undissolved (m.p. 145°–153° C., at 172° C. a clear melt is obtained). It is contaminated with a little 3,4-methylenedioxybenzamide.

EXAMPLE 47

1-(N-p-Phenylbenzoyl-carbamoyl)-2-cyanoaziridine (a) 4-Phenylbenzoyl isocyanate used as starting material is obtained by boiling under reflux for 3 hours 19.7 g. 4-phenylbenzamide (m.p. 223°–224° C.) in 40 ml. ethylene chloride with 19 g. oxalyl chloride, separating off undissolved material, evaporating the filtrate in a vacuum and fractionating the evaporation residue in a vacuum. There are thus obtained 11.4 g. 4-phenylbenzoyl isocyanate; b.p. 148°–154° C./0.01 mm.Hg.

(b) A solution of 0.83 g. 2-cyanoaziridine in 20 ml. toluene is introduced portionwise, while stirring, into a solution of 2.70 g. 4-phenylbenzoyl isocyanate in 40 ml. toluene. The reaction mixture is then stirred for 1 hour at ambient temperature and the precipitated reaction product is filtered off with suction and triturated before with anhydrous diethyl ether to give 2.4 g. 1-(N-p-phenylbenzoyl-carbamoyl)-2-cyanoaziridine; m.p. 168°–172° C.

EXAMPLE 48

The following compounds are prepared in a manner analogous to that described in Example 12:

(a) 1-(N-n-butoxycarbonyl-carbamoyl)-2-cyanoaziridine; m.p. 98°–100° C. from 2-cyanoaziridine and n-butoxycarbonyl isocyanate (b.p. 54°–56° C./15 mm.Hg.);

(b) 1-(N-p-fluorobenzoyl-carbamoyl)-2-cyanoaziridine; m.p. 172°–174° C. from 2-cyanoaziridine and p-fluorobenzoyl isocyanate;

(c) 1-(N-o-methylsulphonylbenzoyl-carbamoyl)-2-cyanoaziridine; m.p. 138°–140° C. from o-methylsulphonylbenzoyl isocyanate (b.p. 152°–154° C./0.1 mm.Hg); and 2-cyanoaziridine (d) 1-(N-methoxyacetyl-carbamoyl)-2-cyanoaziridine; m.p. 136°–138° C. from methoxyacetyl isocyanate (from methoxyacetyl chloride and silver isocyanate) (b.p. 58°–60° C./12 mm.Hg); and 2-cyanoaziridine (e) 1-(N-m-trifluoromethylbenzoyl-carbamoyl)-2-cyanoaziridine; m.p. 158°–160° C. from m-trifluoromethylbenzoyl isocyanate (b.p. 54°–56° C./0.3 mm.Hg); and 2-cyanoaziridine (f) 1-(N-o-methylthiobenzoyl-carbamoyl)-2-cyanoaziridine; m.p. 130°–131° C. from o-methylthiobenzoyl isocyanate (b.p. 130°–132° C./0.3 mm.Hg); and 2-cyanoaziridine (g) 1-(N-cyclopropanecarbonyl-carbamoyl)-2-cyanoaziridine; m.p. 135°–138° C. from cyclopropylcarbonyl isocyanate (from cyclopropyl-carbonyl chloride and silver isocyanate) (b.p. 108°–110° C./500 mm.Hg); and 2-cyanoaziridine (h) 1-(N-cyclobutanecarbonyl-carbamoyl)-2-cyanoaziridine; m.p. 147°–150° C. from cyclobutylcarbonyl isocyanate (from cyclobutyl chloride and silver isocyanate) (b.p. 97° C./120–130 mm.Hg); and 2-cyanoaziridine (i) 1-(N-phenoxycarbonyl-carbamoyl)-2-cyanoaziridine; b.p 134°–136° C. from phenoxycarbonyl isocyanate (b.p. 94°–96° C./14 mm.Hg); and 2-cyanoaziridine (j) 1-(N-phenylacetyl-carbamoyl)-2-cyanoaziridine; m.p. 157°–159° C. from phenylacetyl isocyanate (phenylacetyl chloride and silver isocyanate) (b.p. 62°–66° C./0.3 mm.Hg); and 2-cyanoaziridine (k) 1-(N-diphenylacetyl-carbamoyl)-2-cyanoaziridine; m.p. 156°–158° C. from diphenylacetyl isocyanate (b.p. 158°–160° C./0.5 mm.Hg); and 2-cyanoaziridine (l) 1-phenoxyacetyl-carbamoyl)-2-cyanoaziridine; m.p. 134°–136° C. from phenoxyacetyl isocyanate (b.p. 136° C./1 mm.Hg); and 2-cyanoaziridine (m) 1-(N-acetoxyacetyl-carbamoyl)-2-cyanoaziridine; m.p. 153°–155° C. from acetoxyacetyl isocyanate (b.p. 80°–83° C./14 mm.Hg); and 2-cyanoaziridine (n) 1-(N-p-acetoxybenzoyl-carbamoyl)-2-cyanoaziridine; m.p. 156°–158° C. from p-acetoxybenzoyl isocyanate (b.p. 115° C./0.1 mm.Hg). and 2-cyanoaziridine

EXAMPLE 49

1-N-Dimethoxyphosphoryl-carbamoyl-2-cyanoaziridine

A solution of 3.6 g. dimethoxyphosphoryl isocyanate in 18 ml. anhydrous diethyl ether is added dropwise at 5°–10° C. to a solution of 1.62 g. 2-cyanoaziridine in 36 ml. anhydrous diethyl ether. After stirring for 2 hours in an ice bath, the reaction mixture is allowed to warm to ambient temperature. The precipitated crystals are filtered off with suction and washed with diethyl ether. There is thus obtained 1.85 g. 1-N-dimethoxyphosphoryl-carbamoyl-2-cyanoaziridine; m.p. 72°–76° C. (decomp.).

EXAMPLE 50

N,N'-Ethylphosphonyl-di-(1-carbamoyl-2-cyanoaziridine)

A solution of 1.6 g. ethylphosphonyl diisocyanate in 160 ml. anhydrous diethyl ether is added, with stirring and ice cooling, to a solution of 1.36 g. 2-cyanoaziridine in 40 ml. anhydrous diethyl ether. The white product which separates out is immediately filtered off with suction, washed with diethyl ether and dried. There are thus obtained 2.1 g. of thin layer chromatographically uniform N,N'-ethylphosphonyl-di-(1-carbamoyl-2-cyanoaziridine); m.p. 44°–48° C. (bubbling up).

The pharmacological properties of the new compounds were determined as follows:

Adult female Sprague-Dawley rats of Messrs. WIGA (Gassner, Sulzfeld) weighing 180–220 g were used. The animals were kept at a constant temperature (23±1° C.), constant humidity of the atmosphere (55±5%) and within the 12-hour day/night rhythm. The animals received rat pellets SNIFF of Messrs. intermast, Soest, and water ad libitum. The substances to be tested (dissolved in 10 ml of 0.5% tylose solution per kg of body weight) were once orally applied to 10 rats each time, by means of a throat tube. As control, 10 animals each time were only treated with 10 ml of 0.5% tylose solution per kg of body weight. Prior to the application, the animals were kept fasting and blood was taken from the retroorbital venous plexus by means of a heparinized puncture capillary tube (B 3095/2 of Messrs. Sherwood Med. Inc., St. Louis) and the leucocytes were determined by means of a Coulter counter in known manner.

On the 4th day (except sometimes on the 5th or 7th day, as indicated) blood was again taken from the retroorbital venous plexus and the leucocytes were counted. The averages with standard deviations were ascertained from the individual values. The test groups were only evaluated if the control groups showed no physiological variations. Table 1 shows the value in comparison with the 1-carboxamido-2-cyanoaziridine (BA 1).

The following data show that all tested substances effect a significant increase of the leucocyte number and thus are strongly immune-stimulating.

TABLE

| | Dosage of 200 mg/kg, per os | |
|---|---|---|
| | Leucocytes in Thousands | |
| Active Material of Example | O-Value | Maximum (after 4 days) |
| 3 | 7.8 | 14.9 |
| 4 | 7.7 | 15.3 |
| 28 | 8.5 | 19.8 |
| 2 | 9.3 | 17.3 |
| 5 | 6.7 | 12.7 |
| 21 | 6.3 | 11.0 |
| 20 | 6.9 | 13.7 |
| 19 | 7.4 | 13.6 |
| 17 | 7.9 | 14.7 |
| 11 | 7.1 | 12.0 |
| 9 | 7.6 | 15.7 |
| 7 | 8.5 | 14.3 |
| 48h | 5.6 | 9.8 |
| 48d | 6.4 | 13.1 |
| 50 | 6.8 | 11.8 |
| 35 | 5.5 | 11.9 |
| 48c | 6.0 | 12.0 |
| 48n | 6.1 | 13.3 |
| 48m | 5.4 | 12.3 |
| 48b | 6.8 | 13.6 |
| 48k | 6.1 | 11.1 |
| 48j | 6.3 | 12.3 |
| 33 | 6.1 | 13.1* |
| 48a | 7.6 | 13.5* |
| 10 | 5.4 | 14.5 |
| 46 | 4.9 | 8.6 |
| 45 | 7.5 | 12.6 |
| 44 | 6.7 | 11.5** |
| 18 | 7.6 | 16.7 |
| Comparison 1-Carboxamido-2-cyanoaziridine | 8.9 | 9.5 |
| BA 1 i.v. 500mg/kg | 5.1 | 10.3 |

*After 5 days
**After 7 days

The present invention also provides pharmaceutical compositions comprising the new compound and/or at least one solid or liquid pharmaceutical diluent or carrier.

For the preparation of pharmaceutical compositions, a 1-(N-acyl-carbamoyl)-2-cyanoaziridine in accordance with the invention is mixed in known manner with an appropriate pharmaceutical carrier substance and formed, for example, into tablets or dragees or, with the addition of appropriate adjuvants, suspended or dissolved in water or an oil, for example olive oil, and placed in capsules. Since the active material is acid labile, the composition is provided with a coating which only dissolves in the alkaline medium of the intestines or an appropriate carrier material, for example a high molecular weight fatty acid or carboxymethyl-cellulose is mixed therewith. Examples of solid carrier materials include starch, lactose, mannitol, methyl cellulose, talc, highly dispersed silicic acids, high molecular weight fatty acids (for example stearic acid), gelatin, agar-agar, calcium phosphate, magnesium stearate, animal and vegetable fats and solid high molecular weight polymers (such as polyethylene glycols). Compositions suitable for oral administration can, if desired, contain flavoring and/or sweetening materials.

However, the active material is preferably injected. As injection medium, it is preferred to use water which contains the additives usual in the case of injection solutions, such as stabilizing agents, solubilizing agents and/or weakly alkaline buffers. Additives of this type include, for example, phosphate and carbonate buffers, ethanol, complex-forming agents (for example ethylenediamine-tetraacetic acid and the non-toxic salts thereof) and high molecular weight polymers (for example liquid polyethylene oxide) for viscosity regulation.

For treatment of humans the active material may be applied one or more times with each dose containing about 25 to 3000 and preferably 50 to 500 mg of active material.

It will be appreciated that the instant purification and examples are set forth by way of illustration and not limitation, and that various modifications and changes may be made without departing from the spirit and scope of the present invention.

What is claimed is:

1. Claim (once amended) A 1-(N-acyl-carbamoyl)-2-cyano-aziridine of the formula

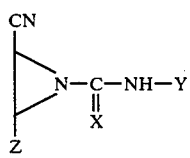

wherein
X is oxygen or sulphur,
Z is hydrogen, alkyl containing up to 4 carbon atoms, and
Y is a —CO—$R_1$, —$SO_2$—$R_2$, —S—$R_3$ or

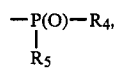

$R_1$ is
(a) hydrogen, nitrile, lower alkoxy, alkoxycarbonyl, N,N-dialkylaminocarbonyl, lower N-alkyl-N-phenyl or N,N-dialkylamino,
(b) aliphatic hydrocarbon saturated or unsaturated optionally substituted once or twice by
 (i) halogen, nitrile, lower N-alkanoylamino, N-N-dialkylamino, alkoxy, alkoxycarbonyl, alkanoyloxy, benzoyloxy, alkylsulphonyloxy, arysulphonyloxy, N,N-dialkylaminocarbonyloxy, alkylsulphonyl or alkylthio,
 (ii) phenyl, naphthyl, phenylthio or phenoxy optionally substituted once or twice by halogen, nitro, phenyl, lower alkyl, alkoxy or alkylthio,
 (iii) dialkoxyphosphoryloxy or dialkoxyphosphono,
 (iv) cycloalkyl, or

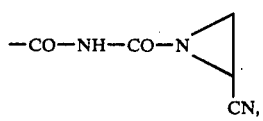

(c) phenyl, phenoxy or optionally hydrogenated naphthyl optionally substituted once or twice by halogen, trifluoromethyl, sulphamoyl, nitro, nitrile, phenyl, lower alkyl, alkylthio, alkylsulphonyl, alkoxy, alkoxycarbonyl, alkoxycarbonylalkyl, N,N-dialkylamino, N,N-dialkylaminocarbonyl, alkanoyl, alkanoyloxy, alkanoyloxyalkyl or methylenedioxy, $R_2$ is (a) a lower aliphatic hydrocarbon radical optionally substituted by halogen, lower alkoxycarbonyl or alkanoyloxy,
(b) cycloalkyl, amino or lower dialkylamino,
(c) phenyl optionally substituted by lower alkyl, lower alkoxy, halogen or nitro, or

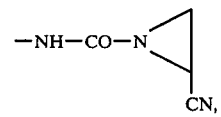

$R_3$ is
(a) lower alkyl on trifluoromethyl, or
(b) phenyl optionally substituted by lower alkyl, halogen or nitro, and $R_4$ and $R_5$ each independently is
(a) lower alkyl or alkoxy,

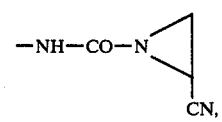

or
$R_4$ and $R_5$ together are alkylenedioxy containing up to 4 carbon atoms, or a pharmacologically compatible salt thereof with a base, when present alkyl having up to 6 carbon atoms, the hydrocarbon substituents containing up to 12 carbon atoms, and cycloalkyl having 3 to 8 ring carbon atoms.

2. 1-[N-(5,6,7,8-Tetrahydronaphthalene-2-carbonyl)-carbamoyl]-2-cyanoaziridine.

3. A compound according to claim 1 wherein such compound is 1-(N-3-nitrobenzoyl-carbamoyl)-2-cyanoaziridine of the formula

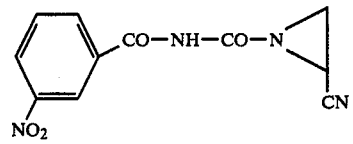

or a pharmacologically compatible salt thereof.

4. A compound according to claim 1 wherein such compound is 1-(N-4-methylbenzenesulphonyl-carbamoyl)-2-cyanoaziridine of the formula

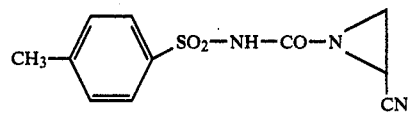

or a pharmacologically compatible salt thereof.

5. A compound according to claim 1 wherein such compound is 1-(N-acryloyl-carbamoyl)-2-cyanoaziridine of the formula

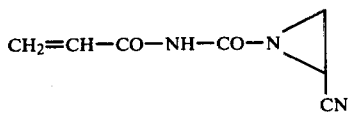

or a pharmacologically compatible salt thereof.

6. A compound according to claim 1 wherein such compound is 1-(N-ethoxycarbonylacetyl-carbamoyl)-2-cyanoaziridine of the formula

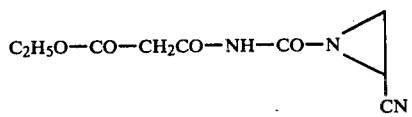

or a pharmacologically compatible salt thereof.

7. A compound according to claim 1 wherein such compound is 1-(N-acetoxyacetyl-carbamoyl)-2-cyanoaziridine of the formula

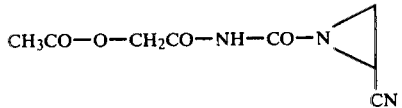

or a pharmacologically compatible salt thereof.

8. A compound according to claim 1 wherein such compound is N,N'-ethylphosphonyl-di-(1-carbamoyl-2-cyanoaziridine) of the formula

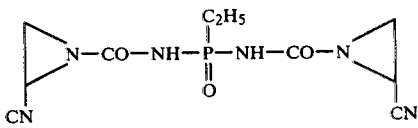

or a pharmacologically compatible salt thereof.

9. An immune-stimulating composition of matter comprising an immune-stimulating effective amount of a compound or salt according to claim 1 in combination with a pharmacologically compatible diluent.

10. The method of stimulating an immune response in a patent comprising administering to the patient an immune-stimulating composition according to claim 9.

11. The method of increasing the number of leucocytes in the system of a patient comprising administering to the patient a composition comprising a pharmacologically acceptable diluent and a leucocyte-increasing effective amount of a compound of salt according to claim 1.

* * * * *